(12) United States Patent
Petisce et al.

(10) Patent No.: US 11,610,674 B2
(45) Date of Patent: Mar. 21, 2023

(54) DIRECT CGM CONNECTIVITY TO A CLOUD STORAGE NETWORK

(71) Applicant: Embecta Corp., Andover, MA (US)

(72) Inventors: James Petisce, Westford, MA (US); Nathaniel McCaffrey, Mill Valley, CA (US)

(73) Assignee: Embecta Corp., Andover, MA (US)

( * ) Notice: Subject to any disclaimer, the term of this patent is extended or adjusted under 35 U.S.C. 154(b) by 78 days.

(21) Appl. No.: 14/775,689

(22) PCT Filed: Mar. 10, 2014

(86) PCT No.: PCT/US2014/022362
§ 371 (c)(1),
(2) Date: Sep. 12, 2015

(87) PCT Pub. No.: WO2014/159174
PCT Pub. Date: Oct. 2, 2014

(65) Prior Publication Data
US 2016/0028821 A1   Jan. 28, 2016

Related U.S. Application Data

(60) Provisional application No. 61/784,858, filed on Mar. 14, 2013.

(51) Int. Cl.
*G06F 15/16*   (2006.01)
*G16H 40/67*   (2018.01)
(Continued)

(52) U.S. Cl.
CPC ........... *G16H 40/67* (2018.01); *A61B 5/0022* (2013.01); *A61B 5/14532* (2013.01);
(Continued)

(58) Field of Classification Search
CPC ..... H04L 67/00; H04L 67/1097; H04L 67/02; A61B 5/0022; A61B 5/14532;
(Continued)

(56) References Cited

U.S. PATENT DOCUMENTS 7,276,029 B2 * 10/2007 Goode, Jr ............ A61B 5/0031
600/300
2007/0253021 A1 11/2007 Mehta et al.
(Continued)

FOREIGN PATENT DOCUMENTS

WO   WO-2012158654 A2   11/2012
WO   WO-2013033655 A1   3/2013

OTHER PUBLICATIONS

C. Doukas and I. Maglogiannis, "Bringing IoT and Cloud Computing towards Pervasive Healthcare," 2012 Sixth International Conference on Innovative Mobile and Internet Services in Ubiquitous Computing, Palermo, 2012, pp. 922-926.*
(Continued)

*Primary Examiner* — Oscar A Louie
*Assistant Examiner* — Messeret F Gebre
(74) *Attorney, Agent, or Firm* — Greenberg Traurig, LLP; David J. Dykeman; Roman Fayerberg (57) ABSTRACT

A system and method is provided for a continuous glucose monitoring (CGM) system and the processing of data collected thereby. An internet gateway chip (140, 240, 340, 440) is included in elements of a CGM system to facilitate direct data communication with cloud network storage (150, 250, 350, 450) thereby communicate and store data of a CGM sensor (110, 210, 310, 410) of the CGM system. The internet gateway chip can be included in a receiver (130, 230, 330), such as an existing wireless receiver and display device of the CGM; in a smart phone or similar device, where the smart phone is also the wireless receiver and
(Continued)

display device of the CGM; or in the sensor, such as an existing sensor and/or transmitter (410, 420) of the CGM to facilitate direct data communication between the CGM system and cloud network storage.

20 Claims, 3 Drawing Sheets

(51) Int. Cl.
*A61B 5/145* (2006.01)
*A61B 5/00* (2006.01)
*G01N 33/66* (2006.01)
*H04L 67/02* (2022.01)
*H04L 67/1097* (2022.01)

(52) U.S. Cl.
CPC ............ *A61B 5/742* (2013.01); *G01N 33/66* (2013.01); *H04L 67/02* (2013.01); *H04L 67/1097* (2013.01); *A61B 5/6898* (2013.01)

(58) Field of Classification Search
CPC ..... A61B 5/002; A61B 5/0024; A61B 5/0031; A61B 5/6846; A61B 5/742; A61B 5/6898; G01N 33/66; G16H 40/67
USPC ........................................................ 709/219
See application file for complete search history.

(56) References Cited

U.S. PATENT DOCUMENTS

| | | | |
|---|---|---|---|
| 2010/0076284 A1 | 3/2010 | Bernstein et al. | |
| 2011/0092164 A1* | 4/2011 | Spanhake | H04W 40/10 455/67.11 |
| 2011/0160544 A1 | 6/2011 | Hayter | |
| 2011/0166875 A1 | 7/2011 | Hayter et al. | |
| 2011/0184264 A1 | 7/2011 | Galasso et al. | |
| 2011/0238235 A1 | 9/2011 | Xia et al. | |
| 2012/0197621 A1 | 8/2012 | Jain | |
| 2012/0220835 A1* | 8/2012 | Chung | A61B 5/0205 600/301 |
| 2012/0246261 A1* | 9/2012 | Roh | G06F 13/385 709/227 |
| 2012/0276894 A1* | 11/2012 | Kai | G06F 19/3418 455/422.1 |
| 2013/0060105 A1 | 3/2013 | Shah et al. | |
| 2013/0097276 A1* | 4/2013 | Sridhar | H04L 67/12 709/217 |
| 2014/0096264 A1* | 4/2014 | Root | G16H 40/67 726/27 |
| 2014/0184422 A1* | 7/2014 | Mensinger | A61B 5/145 340/870.02 |
| 2014/0253323 A1* | 9/2014 | Berven | G08B 21/02 340/539.12 |
| 2014/0288435 A1* | 9/2014 | Richards | A61B 5/14539 600/479 |
| 2017/0303785 A1* | 10/2017 | Mensinger | A61B 5/0004 |
| 2018/0020950 A1* | 1/2018 | Finch | A61B 5/1124 600/595 |

OTHER PUBLICATIONS

H. Nakazawa, M. Ishida and K. Sawada, "Reduction of Interference Between pH and Optical Output Signals in a Multimodal Bio-Image Sensor," in IEEE Sensors Journal, vol. 11, No. 11, pp. 2718-2722, Nov. 2011 (Year: 2011).*

Alaqtash, M., Yu, H., Brower, R., Abdelgawad, A., & Sarkodie-Gyan, T. (2011). Application of wearable sensors for human gait analysis using fuzzy computational algorithm. Engineering Applications of Artificial Intelligence, 24(6), 1018-25 (Year: 2011).*

H. -J. Yoo, J. Yoo and L. Yan, "Wireless fabric patch sensors for wearable healthcare," 2010 Annual International Conference of the IEEE Engineering in Medicine and Biology, 2010, pp. 5254-5257 (Year: 2010).*

\* cited by examiner

DIRECT CGM CONNECTIVITY TO A CLOUD STORAGE NETWORK

CROSS-REFERENCE TO RELATED APPLICATIONS

This application claims the benefit under 35 U.S.C. § 119(a) of U.S. Provisional Application No. 61/784,858, entitled "Direct CGM Connectivity to a Cloud Storage Network", filed Mar. 14, 2013, the entire content of which is incorporated herein by reference.

BACKGROUND OF THE INVENTION

Field of the Invention

The present invention relates to a continuous glucose monitoring (CGM) system and the processing and communication of data collected thereby. The present invention incorporates communication elements with a continuous glucose monitoring system to facilitate direct data communication with cloud network storage to thereby communicate and store data of the CGM sensor without the need for any additional devices or user operations. An internet gateway chip is included with elements of the continuous glucose monitoring system to facilitate direct data communication with cloud network storage.

Description of the Related Art

Blood glucose monitoring is a way of testing the concentration of glucose in the blood. Particularly important in the care of diabetes, a blood glucose test is performed by piercing the skin to draw blood, then applying the blood to a chemically active disposable test strip. Different manufacturers use different technologies, but most systems measure an electrical characteristic of the affected strip, and use this to determine the glucose level in the blood.

In contrast, a continuous glucose monitor (CGM) determines glucose levels on a continuous or periodic basis. A typical system consists of a disposable glucose sensor placed just under the skin, which is worn for a few days until replacement, a link from the sensor to a non-implanted transmitter which communicates to a radio receiver, and an electronic receiver that displays glucose levels with nearly continuous updates, as well as monitors rising and falling trends.

An example of such a system is the Dexcom® SEVEN® PLUS CGM System. The Dexcom system is made up of three components, including a sensor, a transmitter, and a receiver. The receiver can show the user a glucose reading of the sensor at various intervals over a period of uninterrupted wear-time. The Dexcom sensor is a flexible, round, and miniature wire that penetrates just under the skin to read glucose levels at a site, and attaches to the skin with an adhesive patch. The Dexcom transmitter couples with the exposed portion of the sensor and wirelessly sends glucose information to the receiver. The transmitter and built in battery can be coupled with the sensor to form a single, small element that is wireless and lightweight. The adhesive patch holds the coupled transmitter and sensor to the skin. In doing so, the Dexcom receiver provides a wireless device with display and alarm features that displays glucose trends and is a size and weight that allows a user to clip the receiver to a belt, or put it in a pocket or handbag.

In such a system, CGM sensors provide a tremendous amount of data that, for example, can be used to develop trending information of its end user's glucose concentrations over the entire course of several days of sensor use. Such information is of utility to healthcare providers such as endocrinologists or nurse practitioners because such CGM data trends can be used to optimize therapies and treatments being administered to an end user in order to achieve glycemic control. Additionally, CGM sensor data can be utilized to provide caregivers, such as parents of young children or custodians of elderly people, access to the sensor end users' glucose control.

However, there is a need with currently available systems and methods for a means to easily present to others the ability to view the CGM sensor output and access the quality of glycemic control the sensor end user is achieving. One solution to such a need is the collection and storage of such data in a manner that is accessible by others. In one system, outputs from commercially available CGM sensors can be downloaded to a personal computer by the end user or end user's healthcare provider. Unfortunately, this option is so cumbersome that recent data from the T1D Exchange indicates that only a small number of end user's data is managed in this way.

The recent availability of data storage in cloud network form affords another possibility to collect and store such data in a manner that is accessible by others, such as utilizing cloud network storage as a storage and access medium for the large quantity of data acquired by a CGM sensor system and which can be accessible by others. There are several possible modes of connectivity to such cloud storage networks. Borrowing again from the information harvested from the T1D Exchange data regarding the downloading of CGM sensor data to a personal computer, end user ease-of-use dictates whether a specific mode of connectivity to a cloud storage network will be utilized. Data from CGM systems is currently being uploaded to cloud storage networks such as Medtronic's Carelink, the T1D Exchange or Dexcom's SweetSpot, but requires additional equipment and significant additional user operations. For example, storage is accomplished by first downloading CGM data to a computer file and then uploading it to a cloud storage network. One other commercially available CGM supplier recently announced that glucose data from its sensor would be relayed to a cloud storage network via an internet hub. In this case, such system architecture would require the CGM sensor end user to carry an additional device to connect to a cloud storage network. In each case, end users are less likely to take advantage of these features due to the additional inconveniences.

Accordingly, there is a need for a system and method to connect a CGM sensor or similar device directly to a cloud storage network to thereby communicate and store data of the CGM sensor without the need for any additional devices or user operations.

SUMMARY OF THE INVENTION

Exemplary embodiments of the present invention address the above and other issues, and provide a system and method to connect a CGM sensor or similar device directly to a cloud storage network to thereby communicate and store data of the CGM sensor without the need for any additional devices or user operations. Such a system and method enables the CGM sensor end user to have the ability to connect to cloud storage networks without the burden of carrying an internet hub or requiring additional user operations.

Another aspect of exemplary embodiments of the present invention is to provide a system and method to incorporate communication elements with a continuous glucose monitoring system to facilitate direct data communication with cloud network storage. In an exemplary embodiment, an internet gateway chip is included in elements of a continuous glucose monitoring system to facilitate direct data communication with cloud network storage.

Another aspect of exemplary embodiments of the present invention is to provide a system and method to incorporate such an internet gateway chip in a receiver of the CGM, such as an existing wireless receiver and display device of the CGM.

Another aspect of exemplary embodiments of the present invention is to provide a system and method to incorporate such an internet gateway chip in a smart phone or similar device, where the smart phone is also the wireless receiver and display device of the CGM.

Another aspect of exemplary embodiments of the present invention is to provide a system and method to incorporate such an internet gateway chip in a sensor, such as an existing sensor and/or transmitter of the CGM.

To substantially achieve these and other aspects of the present invention, a system and method is provided to incorporate communication elements such as an internet gateway chip with one or more elements of a CGM system to facilitate direct data communication with cloud network storage without the need for any additional devices or user operations.

BRIEF DESCRIPTIONS OF THE DRAWINGS

These and other objects, advantages and novel features of the invention will become more readily appreciated from the following detailed description when read in conjunction with the accompanying drawings, in which.

Throughout the drawings, like reference numerals will be understood to refer to like parts, components and structures.

DETAILED DESCRIPTION OF EXEMPLARY EMBODIMENTS

As shown in the attached drawing figures, exemplary embodiments of the present invention provide a system and method to connect a CGM sensor or similar device directly to a cloud storage network to thereby communicate and store data of the CGM sensor in a manner that permits CGM data to be accessible by others and without the need for any additional devices or user operations. Such a system and method enables the CGM sensor end user to have the ability to connect to cloud storage networks without the burden of carrying an internet hub or requiring additional user operations. To do so, exemplary embodiments incorporate an internet gateway chip with elements of a CGM system to facilitate direct data communication with cloud network storage. More specifically, the exemplary embodiments provide an internet gateway chip in a receiver, such as an existing wireless receiver and display device of the CGM; in a smart phone or similar device, where the smart phone is also the wireless receiver and display device of the CGM; or in the sensor, such as an existing sensor and/or transmitter of the CGM.

Accordingly, exemplary embodiments of the present invention address the above and other issues, and provide a system and method to connect a CGM sensor or similar device directly to a cloud storage network to thereby communicate and store data of the CGM sensor in a manner that permits CGM data to be accessible by others and without the need for any additional devices or user operations. Such a system and method enables the CGM sensor end user to have the ability to connect to cloud storage networks without the burden of carrying an internet hub or requiring additional user operations.

Figure 1:
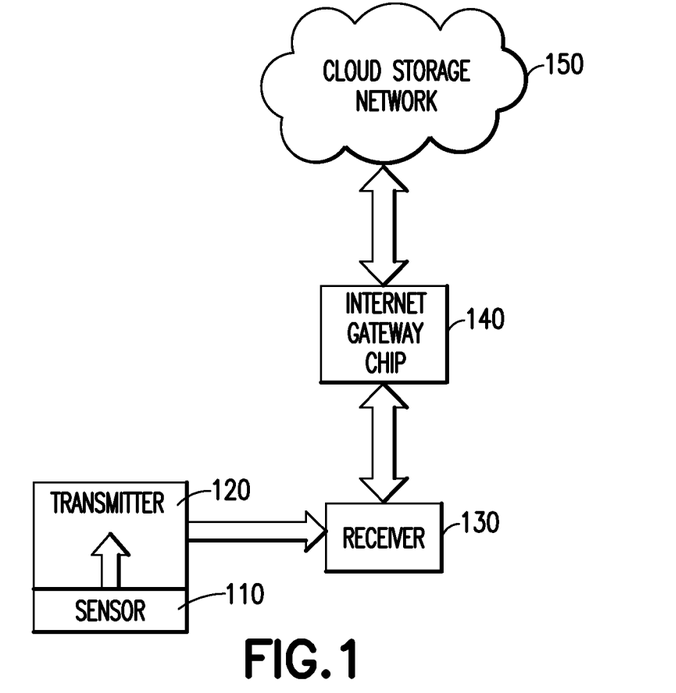
FIG. 1 is a block diagram of a system to incorporate communication elements such as an internet gateway chip with one or more elements of a CGM system to facilitate direct data communication with cloud network storage in accordance with an embodiment of the present invention.

FIG. 1 is a block diagram of a system to incorporate communication elements such as an internet gateway chip with one or more elements of a CGM system to facilitate direct data communication with cloud network storage in accordance with an embodiment of the present invention. A CGM system determines glucose levels on a continuous or periodic basis, and a typical system consists of a disposable glucose sensor placed just under the skin, which is worn for a few days until replacement, a link from the sensor to a non-implanted transmitter which communicates to a radio receiver, and an electronic receiver that displays glucose levels with nearly continuous updates, as well as monitors rising and falling trends. An example of such a system is the Dexcom® SEVEN® PLUS CGM System which is made up of three such components, including a sensor, a transmitter, and a receiver. The receiver can display or show the user information such as a glucose reading at various intervals over a period of uninterrupted wear-time. The Dexcom sensor is a flexible, round, and miniature wire that penetrates just under the skin to read glucose levels at a site, and attaches to the skin with an adhesive patch. The Dexcom transmitter couples with the exposed portion of the sensor and wirelessly sends glucose information to the receiver. The transmitter and built in battery can be coupled with the sensor to form a single, small element that is wireless and lightweight, and an adhesive patch can be used to hold the coupled transmitter and sensor to the skin. However, in exemplary embodiments of the present invention, these or any other type of invasive, non-invasive or minimally invasive CGM sensing technology can be used in the practice of the present invention. Exemplary disclosures of CGM sensors, such as those employing glucose binding protein (GBP), can be found in the following published international (PCT) patent applications: WO 2006/044973, published Apr. 27, 2006; WO 2007/124464, published Nov. 1, 2007; and WO 2008/131360, published Oct. 30, 2008, the entire contents of all of which are incorporated herein by reference.

In accordance with the present invention, an internet gateway chip or similar internet gateway chip system can be provided in a number of different CGM configurations each resulting in providing communication between a CGM element and a cloud storage network. In the embodiment of FIG. 1, the CGM system is made up of three components, including a sensor 110, transmitter 120 and receiver and display device 130. The receiver and display device 130 includes various user controls and a display to show the user glucose or other variable readings during the wear-time of the sensor 110. The sensor 110 can be any suitable sensor such as provided by a flexible, round, miniature wire or other element that penetrates the skin to read glucose levels at a site, and attaches to the skin such as with an adhesive patch. The transmitter 120 can be coupled with or otherwise incorporated with an exposed portion of the sensor 110, and can wirelessly send glucose information obtained from the sensor 110 to the receiver and display device 130. The transmitter 120 can further include a battery or other power supply (not shown) to power the transmitter 120 and sensor 110. An adhesive layer or other attachment means can be provided to hold the transmitter and sensor in position on a skin surface.

In exemplary embodiments of the present invention, the internet gateway chip system or internet gateway chip can be incorporated into one or more of the elements of the CGM system and/or used to replace one or more of the elements of an existing CGM system. In the following examples, the internet gateway chip system or internet gateway chip 140, 240, 340 and 440 can comprise, for example, a single-chip RF Processing device including but not limited to, Qualcomm WCDMA/HSPA+ devices, Siena Wireless, Infineon, TI, Freescale, ST Micro, MedioTek and Marvel internet gateway devices. Still other applicable internet gateway devices include those manufactured by companies such as Centurion, Telit, SIMCom, Ericsson, and others. Further, in any of the exemplary embodiments of the present invention, the internet gateway chip system or internet gateway chip 140, 240, 340 and 440 can comprise dedicated chips to communicate with separate or selectable cloud storage networks, respectively. Bidirectional communication of the internet gateway chip system or internet gateway chip 140, 240, 340 and 440 can be provided via any number of means such as but not limited to RF, Bluetooth and infrared communication, and others as specified under the IEEE 802 wireless standards, including but not limited to 802.11 (WiFi, WLAN), 802.15 (WPAN, Bluetooth, ZigBee) and 802.16 (WMAN).

In the embodiment of FIG. 1, the sensor 110 continuously monitors a blood glucose level or other variables at a site, and the measurements of the sensor 110 are processed for transmission and transmitted by the transmitter 120 to the receiver and display device 130. Communication between the transmitter 120 and the receiver and display device 130 can be provided via any number of wired communication means such as USB and Firewire connections, and wireless communication means such as RF, Bluetooth and infrared communication, and others as specified under the IEEE 802 wireless standards, including but not limited to 802.11 (WiFi, WLAN), 802.15 (WPAN, Bluetooth, ZigBee) and 802.16 (WMAN). The receiver 130 can buffer, store and/or display the sensor data in any number of desired fashions. Further, the data of the receiver 130 can be downloaded to a personal computer by the end user or end user's healthcare provider. Still further, the glucose data from the sensor can be relayed to the cloud storage network via an internet hub. However, exemplary embodiments of the present invention utilize an internet gateway chip 140 in a manner to allow the user to connect a CGM sensor or similar device directly to a cloud storage network to thereby communicate and store data of the CGM sensor without the need for any additional devices or user operations. The internet gateway chip 140 further enables the end user to access data of the cloud storage network 150.

Cloud storage is a model of networked online storage where data is stored in virtualized storage pools which are generally hosted by third parties. Hosting companies operate large data centers, and users who require their data to be hosted buy or lease storage capacity. The data center operators, in the background, virtualize the resources according to the requirements of the customer and expose them as storage pools, which the customers can themselves use to store files or data objects. Physically, the resource may span across multiple servers, and the safety of the files depends upon the hosting websites. Such cloud storage services may be accessed through a web service application programming interface (API), a cloud storage gateway or a Web-based user interface. In the case of the present invention, cloud storage of sensor data allows the end user and others the ability to access and view the CGM sensor output and study the quality of glycemic control that the sensor end user is achieving.

Data from CGM systems is currently being uploaded to cloud storage networks such as Medtronic's Carelink, the T1D Exchange or Dexcom's SweetSpot. However, in the case of these systems, storage is accomplished by first downloading CGM data to a computer file and then uploading it to a cloud storage network. One commercially available CGM supplier employs a system wherein glucose data from its sensor is relayed to a cloud storage network via an internet hub. Such system architectures require the CGM sensor end user to carry an additional device to connect to a cloud storage network and in each case, end users are less likely to take advantage of these features due to the additional inconveniences. However, exemplary embodiments of the present invention utilize an internet gateway chip 140 in a manner to allow the user to connect a CGM sensor or similar device directly to a cloud storage network via the receiver and display device 130 to thereby communicate and store data of the CGM sensor without the need for any additional devices or user operations.

Figure 2:
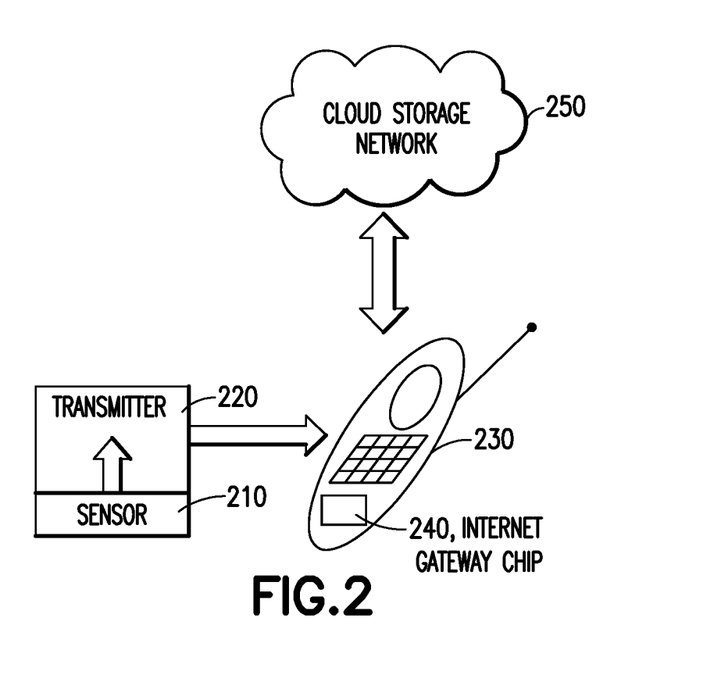
FIG. 2 is a block diagram of a system to incorporate an internet gateway chip in a smart phone or similar device, where the smart phone is also the wireless receiver and display device of the CGM in accordance with another embodiment of the present invention.

FIG. 2 is a block diagram of a system to incorporate an internet gateway chip in a mobile communication terminal, such as a smart phone or similar device, where the smart phone is also the wireless receiver and display device of the CGM in accordance with another embodiment of the present invention. In the embodiment of FIG. 2, an internet gateway chip 240 is incorporated with a smart phone or similar device, where the smart phone is also the receiver and display device 230 of the CGM in accordance with an embodiment of the present invention. In an exemplary embodiment of the present invention, the mobile communication terminal can include any of a cellular telephone, smart phone, programmable cellular telephone, portable computer, receiver associated with a retransmitter, smart phone, or personal digital assistant (PDA). Other examples of a wired or wireless hand-held communication element, receiver and display device 230 can include but are not limited to an iPhone™, Android™, iPad™, Blackberry™, or the like. The exemplary embodiment of the present invention of FIG. 2 provides the internet gateway chip incorporated into the smart phone-like receiver and display device 230, to enable the end user to connect the CGM sensor output directly to the cloud storage network via their smart phone. In an exemplary embodiment, the smart phone also serves as an input, control and display device for the CGM sensor output received from the sensor and receiver of the CGM system.

In the embodiment of FIG. 2, the CGM system comprises a sensor 210, transmitter 220 and receiver and display device 230. The sensor 210 and transmitter 220 are substantially the same as sensor 110 and transmitter 120 as described above. The receiver and display device 230 includes various user controls and a display to show the user glucose or other variable readings during the wear-time of the sensor 210. An internet gateway chip 240 or similar device is provided in a configuration that results in providing communication between the CGM element and a cloud storage network 250. The cloud storage network 250 is substantially the same as cloud storage network 150 as described above. The receiver and display device 230 comprises a smart phone or similar device, where the smart phone is also the wireless display device of the CGM. The internet gateway chip 240 is incorporated into the smart phone-like device 230, to enable the end user to connect the CGM sensor output directly to the cloud storage network 250 via their smart phone.

In the embodiment of FIG. 2, the sensor 210 continuously monitors a blood glucose level or other variable at a site. The measurements of the sensor 210 are processed for transmission and transmitted by the transmitter 220 to the smart phone-like receiver and display device 230. Bidirectional communication between the transmitter 220 and the smart phone-like receiver and display device 230 can be provided via any number of wired communication means such as USB and Firewire connections, and wireless communication means such as RF, Bluetooth and infrared communication, and others as specified under the IEEE 802 wireless standards, including but not limited to 802.11 (WiFi, WLAN), 802.15 (WPAN, Bluetooth, ZigBee) and 802.16 (WMAN). The smart phone-like receiver and display device 230 can buffer, store and/or display the sensor data in any number of desired fashions.

The smart phone-like receiver and display device 230 includes the internet gateway chip 240 and/or a web service application programming interface (API), a cloud storage gateway or a Web-based user interface. In doing so, the internet gateway chip 240 enables the end user to connect the CGM sensor output directly to the cloud storage network 250 via their smart phone. The internet gateway chip 240 further enables the end user to access data of the cloud storage network 250 via their smart phone. The glucose data from the sensor 210 can be relayed to the cloud storage network 250 without the need for an internet hub or additional user operations. Accordingly the exemplary embodiment of the present invention allows the user to connect a CGM sensor or similar device directly to a cloud storage network to thereby communicate and store data of the CGM sensor without the need for any additional devices or user operations.

Figure 3:
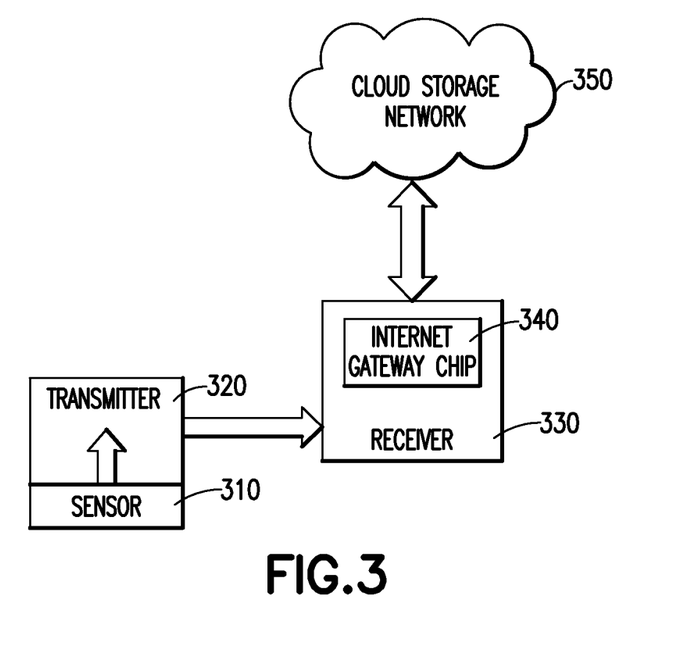
FIG. 3 is a block diagram of a system to incorporate an internet gateway chip in a receiver of the CGM, such as an existing wireless receiver and display device of the CGM in accordance with another embodiment of the present invention.

FIG. 3 is a block diagram of a system to incorporate an internet gateway chip in a receiver of the CGM, such as an existing wireless receiver and display device of the CGM in accordance with another embodiment of the present invention. In the embodiment of FIG. 3, an internet gateway chip 340 is incorporated with a receiver and display device, which is preferably an existing receiver and display device of the CGM in accordance with an embodiment of the present invention. An exemplary embodiment of the present invention provides an internet gateway chip incorporated into the receiver and display device of the CGM sensor system. As noted, CGM sensor systems can utilize a small, hand-held device as a receiver and display device 330, which displays the output from its sensor in a real-time fashion. Embedding a gateway chip 340 directly into the CGM sensor system receiver and display device 330 allows the end user to transfer their sensor data directly into a cloud storage network without the need to carry any extra devices while using their CGM sensor system.

In the embodiment of FIG. 3, the CGM system comprises a sensor 310, transmitter 320 and receiver and display device 330. The sensor 310 and transmitter 320 are substantially the same as sensor 110 and transmitter 120 as described above. The receiver and display device 330 includes various user controls and a display to show the user glucose or other variable readings during the wear-time of the sensor 310. An internet gateway chip 340 or similar device is provided in a configuration that results in providing communication between the CGM element and a cloud storage network 350. The cloud storage network 350 is substantially the same as cloud storage network 150 as described above. The internet gateway chip 340 is incorporated into the receiver and display device 330 to enable the end user to connect the CGM sensor output directly to the cloud storage network 350 via their receiver and display device. The internet gateway chip 340 further enables the end user to access data of the cloud storage network 350 via their receiver and display device.

In the embodiment of FIG. 3, the sensor 310 continuously monitors a blood glucose level or other variable at a site. The measurements of the sensor 310 are processed for transmission and transmitted by the transmitter 320 to the receiver and display device 330. Communication between the transmitter 320 and the receiver and display device 330 can be provided via any number of wired communication means such as USB and Firewire connections, and wireless communication means such as RF, Bluetooth and infrared communication, and others as specified under the IEEE 802 wireless standards, including but not limited to 802.11 (WiFi, WLAN), 802.15 (WPAN, Bluetooth, ZigBee) and 802.16 (WMAN). The receiver 330 can buffer, store and/or display the sensor data in any number of desired fashions.

The receiver and display device 330 includes the internet gateway chip 340 and/or a web service application programming interface (API), a cloud storage gateway or a Web-based user interface. In doing so, the internet gateway chip 340 enables the end user to connect the CGM sensor output directly to the cloud storage network 350 via their receiver. The glucose data from the sensor 310 can be relayed to the cloud storage network 350 without the need for an internet hub. Accordingly the exemplary embodiment of the present invention allows the user to connect a CGM sensor or similar device directly to a cloud storage network to thereby communicate and store data of the CGM sensor without the need for any additional devices or user operations.

Figure 4:
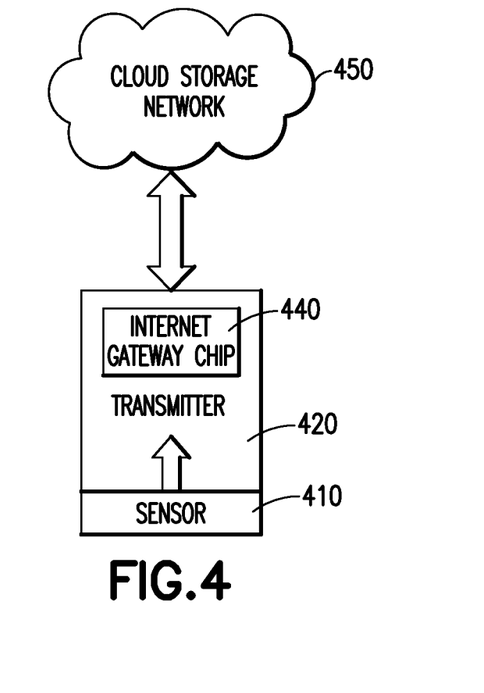
FIG. 4 is a block diagram of a system to incorporate an internet gateway chip in a sensor, that is, an existing sensor and/or transmitter of the CGM in accordance with another embodiment of the present invention.

In the embodiment of FIG. 4, an internet gateway chip 440 is incorporated in a sensor, which is preferably an existing sensor and/or transmitter of the CGM in accordance with an embodiment of the present invention. An exemplary embodiment of the present invention provides an internet gateway chip incorporated into the CGM sensor itself. In this system architecture, the sensor output could be transmitted directly from the sensor and transmitter to a cloud storage network and further, the data display device commonly used with commercially available CGM systems on the market today may not be needed. Specifically, once CGM sensor data is transferred into a cloud storage network, the end user could choose the most convenient time and mode of viewing their sensor data by accessing it on the cloud storage network.

FIG. 4 is a block diagram of a system to incorporate an internet gateway chip in a sensor, that is, an existing sensor and/or transmitter of the CGM in accordance with another embodiment of the present invention. In the embodiment of FIG. 4, the system comprises a sensor 410 and transmitter 420. The sensor 410 and transmitter 420 are substantially the same as sensor 110 and transmitter 120 as described above, but having the incorporation of an internet gateway chip and excluding the need for a receiver and display device. However, a receiver and display device can be provided with the embodiment of FIG. 4 if desired for command, display or other operations. An internet gateway chip 440 or similar device is provided in a configuration that results in providing communication between the CGM element and a cloud storage network 450. The cloud storage network 450 is substantially the same as cloud storage network 150 as described above. The internet gateway chip 440 is incorporated into the sensor 410 and/or transmitter 420, to enable the end user to connect the CGM sensor output directly to the cloud storage network 450 via their sensor 410 and/or transmitter 420.

In the embodiment of FIG. 4, the sensor 410 continuously monitors a blood glucose level or other variable at a site. The measurements of the sensor 410 are processed for transmission and transmitted by the transmitter 420. The sensor 410 and/or transmitter 420 include the internet gateway chip 440 and/or a web service application programming interface (API), a cloud storage gateway or a Web-based user interface. In doing so, the internet gateway chip 440 enables the end user to connect the CGM sensor output directly to the cloud storage network 450 via their sensor and/or transmitter. The glucose data from the sensor 410 can be relayed to the cloud storage network 450 without the need for an internet hub or user operations. The measurements of the sensor 410 can also be processed for transmission and transmitted by the transmitter 420 to a receiver and display device if provided, in addition to the transmission to the cloud storage network 450. Accordingly the exemplary embodiment of the present invention allows the user to connect a CGM sensor or similar device directly to a cloud storage network to thereby communicate and store data of the CGM sensor without the need for any additional devices or user operations.

Figure 5:
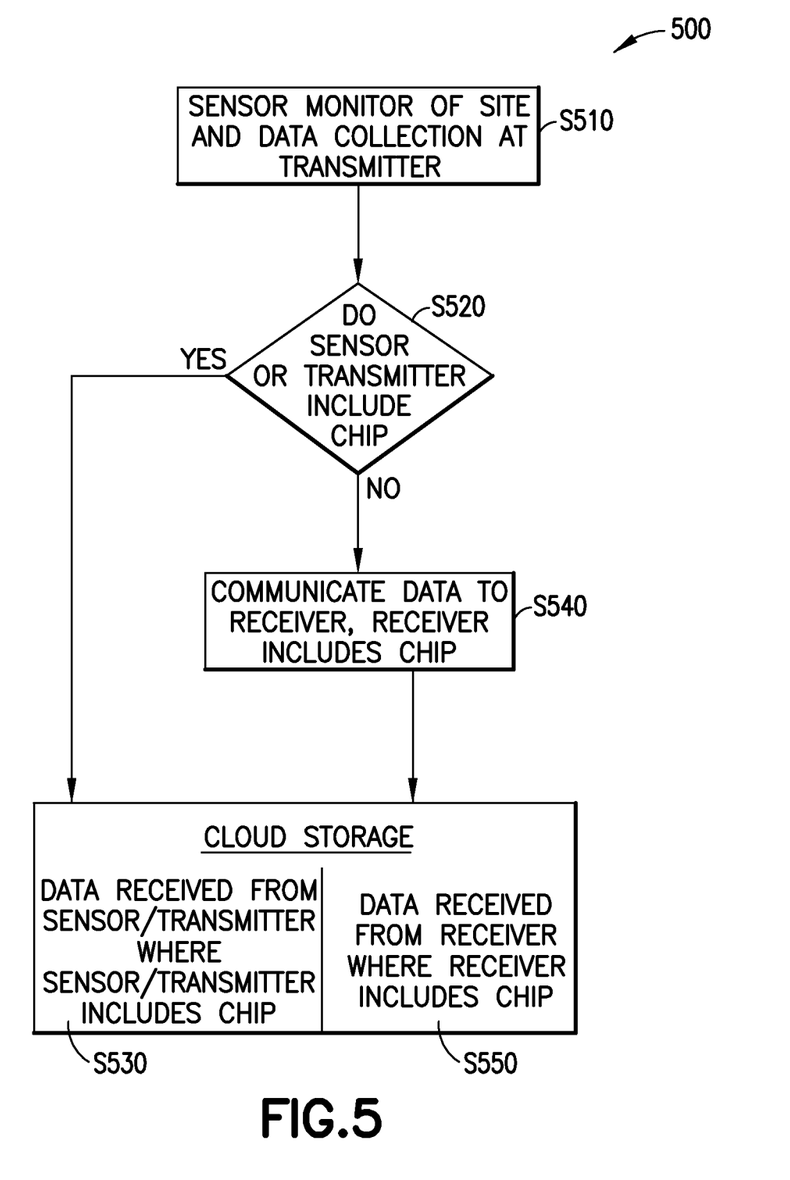
FIG. 5 is a flow chart of a method to use communication elements such as an internet gateway chip with one or more elements of a CGM system to facilitate direct data communication with cloud network storage in accordance with an embodiment of the present invention.

FIG. 5 is a flow chart of a method to use communication elements such as an internet gateway chip with one or more elements of a CGM system to facilitate direct data communication with cloud network storage in accordance with an embodiment of the present invention. The method 500 comprises a first step S510 for continuously, periodically or episodically monitoring a blood glucose level or other variable at a site, such as performed by the sensors 110, 210, 310 and 410. The measurements of the sensor are then processed for transmission, such as performed by the transmitters 120, 220, 320 and 420. If the sensor, such as sensor 410 and/or transmitter 420, is found to include an internet gateway chip, such as internet gateway chip 440, and/or a web service application programming interface (API), a cloud storage gateway or a Web-based user interface at S520, the data can be relayed from the sensor and/or transmitter directly to the cloud storage network at S530.

If the sensor, such as sensors 110, 210 and 310 and/or transmitters 120, 220 and 320, is found to not include an internet gateway chip at S520, the data is transmitted by the transmitter to a receiver or smart phone-like device, such as devices 130, 230 and 330 at S540. If the receiver or smart phone-like device is found to include an internet gateway chip, such as internet gateway chips 140, 240 and 340, and/or a web service application programming interface (API), a cloud storage gateway or a Web-based user interface, the data can be relayed from the receiver or smart phone-like device directly to the cloud storage network at S550.

The internet gateway chip system or internet gateway chips 140, 240, 340, 440 can further comprise dedicated chips to communicate with separate cloud storage networks, respectively. Further, the provision of the direct data communication with the cloud network storage or access to the communicated data of the cloud network storage can be restricted, and require user registration, password entry, and/or fee payment.

Accordingly, exemplary embodiments of the present invention provide a system and method to connect a CGM sensor or similar device directly to a cloud storage network to thereby communicate and store data of the CGM sensor in a manner that permits CGM data to be accessible by others and without the need for any additional devices or user operations. Such a system enables the CGM sensor end user to have the ability to connect the CGM sensor to a cloud storage network without the burden of carrying an internet hub to communicate and store data of the CGM sensor or require additional user operations. The system and method incorporates communication elements with a CGM system to facilitate direct data communication with cloud network storage. An internet gateway chip is included in elements of the CGM system to facilitate direct data communication with cloud network storage. For example, such an internet gateway chip can be included in a receiver, such as an existing wireless receiver and display device of the CGM; in a smart phone or similar device, where the smart phone is also the wireless receiver and display device of the CGM; or in the sensor, such as an existing sensor and/or transmitter of the CGM. Exemplary embodiments of the present invention can be applied in a number of devices and components including, for example, a CGM receiver that has an embedded gateway chip enabling direct cloud connectivity, a CGM receiver that has CGM data display capabilities, a CGM receiver replaced with a cellphone or smart phone-like device having an embedded gateway chip enabling direct cloud connectivity, and a CGM on-body sensor (OBS) that has an embedded gateway chip enabling direct cloud connectivity.

The exemplary embodiments described above provide a system and method of data collection at a CGM sensor, communication of data from the sensor to either a receiver and/or cell phone having an embedded gateway chip and thereafter directly to a cloud storage network, or where the sensor has an embedded gateway chip, directly to a cloud storage network, to thereby store data of the CGM sensor. The CGM data is acquired and transmitted preferably without any manual operations. In an exemplary embodiment, the data is transmitted to a cloud storage network for storage, processing and retrieval, again, preferably without any manual operations. In doing so, there is no need for data transmission to a CGM receiver where the sensor has an embedded gateway chip, nor the data transmission to or through an internet hub where the receiver/cell phone has an embedded gateway chip. Further, there is no need for a user to direct the communication of data using manual operations nor communicate the data in an intermediate manner such as, for example, downloading data from a receiver to a computer or uploading data from a computer to cloud storage.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims and their equivalents.

The invention claimed is:

1. A system to communicate data of a continuous glucose monitor (CGM) sensor, the system comprising:
   a CGM element for measuring glucose measurement data and communicating said glucose measurement data to a cloud storage network;
   the CGM element comprising a sensor, a controller, and a transmitter coupled to an exposed portion of the sensor, wherein the CGM element comprises stored executable program instructions executable by the controller such that the system is programmed to:
      determine whether the CGM element includes an internet gateway chip;
      in response to determining that the CGM element includes the internet gateway chip, configure the CGM element to control the transmitter to transmit the glucose measurement data directly to the cloud storage network; and
      in response to determining that the CGM element does not include the internet gateway chip, configure the CGM element to control the transmitter to transmit the glucose measurement data to a receiver and display device; and
   wherein the transmitter and the receiver and display device are configured to establish direct data communication with cloud network storage, and to receive said glucose measurement data of said CGM element and communicate said glucose measurement data to said cloud network storage via said direct data communication with said cloud network storage without user interactions.

2. The system of claim 1, wherein said receiver and display device comprises at least one internet gateway chip.

3. The system of claim 2, wherein said internet gateway chip is incorporated with said sensor.

4. The system of claim 1, wherein said receiver and display device comprises a web service application programming interface (API), a cloud storage gateway or a Web-based user interface.

5. The system of claim 2, wherein said CGM element comprises a mobile communication terminal, wherein said mobile communication terminal comprises a wireless display device and wherein said internet gateway chip is incorporated with said mobile communication terminal.

6. The system of claim 2, wherein said CGM element comprises a receiver of an existing wireless display device and wherein said internet gateway chip is incorporated with said receiver.

7. A method to communicate data of a continuous glucose monitor (CGM) sensor, the method comprising:
   providing a CGM element comprising a sensor, a controller, stored executable program instructions, and at least one transmitter coupled to an exposed portion of the sensor to provide direct data communication with cloud network storage;
   controlling said CGM element according to the stored executable program instructions to:
      continuously, periodically or episodically monitor a glucose level at a site and process glucose measurement data based on said glucose level of said sensor for transmission,
      determine whether said sensor includes an internet gateway device,
      in response to determining that the sensor includes the internet gateway device, configure the CGM element to transmit said glucose measurement data of said sensor to said cloud network storage via said internet gateway device,
      in response to determining that said sensor does not include the internet gateway device, configure the CGM element to control said sensor to transmit said glucose measurement data to a receiver or mobile communication terminal that includes said internet gateway device, and
      controlling said receiver or said mobile communication terminal to transmit said glucose measurement data to said cloud network storage via said receiver or said mobile communication terminal without user interactions.

8. The method of claim 7, wherein said at least one transmitter transmits to the receiver comprising the internet gateway device.

9. The method of claim 8, wherein said internet gateway device communicates with separate cloud storage networks.

10. The method of claim 8, wherein said internet gateway device is incorporated with said sensor.

11. The method of claim 7, wherein said CGM element comprises a web service application programming interface (API), a cloud storage gateway or a Web-based user interface.

12. The method of claim 8, wherein said CGM element comprises a wireless display device and wherein said internet gateway device is incorporated with said mobile communication terminal.

13. The method of claim 8, wherein said CGM element comprises a receiver of an existing wireless display device and wherein said internet gateway device is incorporated with said receiver.

14. The method of claim 7, wherein at least one of direct data communication with cloud network storage and access to data of cloud network storage is provided in response to a user registration.

15. The method of claim 7, wherein at least one of direct data communication with cloud network storage and access to data of cloud network storage is provided in response to a user fee payment.

16. A system to communicate data of a continuous glucose monitor (CGM) sensor, the system comprising:
   a glucose sensor, a controller, stored executable program instructions, and a data transmitter coupled to an exposed portion of the glucose sensor, for measuring glucose measurement data and communicating said glucose measurement data to at least one internet gateway device;
   the stored executable program instructions are executable by the controller to cause the controller to:
      determine whether the CGM sensor includes an internet gateway device;
      in response to determining that the CGM sensor includes the internet gateway device, configure the CGM sensor to control the data transmitter to transmit the glucose measurement data directly to a cloud storage network;
      in response to determining that the CGM sensor does not include the internet gateway device, configure the CGM sensor to control the data transmitter to transmit the glucose measurement data to a receiver and display device having the internet gateway device without user interactions.

17. The system of claim 16, wherein said internet gateway device comprises at least one of an internet gateway chip, a web service application programming interface (API), a cloud storage gateway, or a Web-based user interface.

18. The system of claim 17, further comprising a mobile communication terminal, wherein said mobile communication terminal comprises a wireless display device and wherein said internet gateway device is incorporated with said mobile communication terminal.

19. The system of claim 17, further comprising a receiver of an existing wireless display device and wherein said internet gateway device is incorporated with said receiver.

20. The system of claim 17, further comprising an existing sensor and transmitter and wherein said internet gateway device is incorporated with said existing sensor.

* * * * *